(12) United States Patent
Freiherr Von Der Goltz

(10) Patent No.: US 7,223,365 B2
(45) Date of Patent: May 29, 2007

(54) DEVICE AND METHOD FOR DETECTING THE COAGULATION FUNCTIONS OF GLOBAL, ESPECIALLY PRIMARY HEMOSTASIS

(76) Inventor: Volker Freiherr Von Der Goltz, Michael Haydn Weg 1, Seeon 83370 (DE)

( * ) Notice: Subject to any disclaimer, the term of this patent is extended or adjusted under 35 U.S.C. 154(b) by 810 days.

(21) Appl. No.: 10/182,238

(22) PCT Filed: Jan. 24, 2001

(86) PCT No.: PCT/EP01/00763

§ 371 (c)(1),
(2), (4) Date: Nov. 18, 2002

(87) PCT Pub. No.: WO01/55715

PCT Pub. Date: Aug. 2, 2001

(65) Prior Publication Data

US 2003/0130596 A1    Jul. 10, 2003

(30) Foreign Application Priority Data

Jan. 25, 2000   (DE) ................... 100 03 093

(51) Int. Cl.
*G01N 15/06* (2006.01)
*G01N 33/86* (2006.01)
*G01N 33/00* (2006.01)
*A61B 8/00* (2006.01)
*A61B 8/14* (2006.01)

(52) U.S. Cl. ............. 422/68.1; 436/69; 422/73; 600/454; 600/468

(58) Field of Classification Search ........... 436/69; 422/73; 128/637, 771

See application file for complete search history.

(56) References Cited

U.S. PATENT DOCUMENTS

| | | | |
|---|---|---|---|
| 5,275,953 A | 1/1994 | Bull | |
| 5,339,830 A | 8/1994 | Blake, III | |
| 5,599,718 A | 2/1997 | Gorog | |
| 5,662,107 A | 9/1997 | Sakariassen | |
| 5,925,569 A * | 7/1999 | Gorog et al. | 436/69 |
| 6,004,819 A | 12/1999 | Gorog et al. | |

FOREIGN PATENT DOCUMENTS

DE    196 17 407    11/1997

* cited by examiner

*Primary Examiner*—Jill Warden
*Assistant Examiner*—Neil Turk
(74) *Attorney, Agent, or Firm*—Crowell & Moring LLP

(57) ABSTRACT

A method and a device are provided for examining the properties of the global, in particular the primary, hemostasis functions in whole blood or platelet-rich plasma. A volumetric blood flow is preferably adjusted, depending on the measured pressure of the volumetric flow, so that the shear rate or the shear force, whose action in the reaction opening causes blood components, in particular thrombocytes, to deposit, follows a predetermined characteristic curve and in particular is held constant.

8 Claims, 8 Drawing Sheets

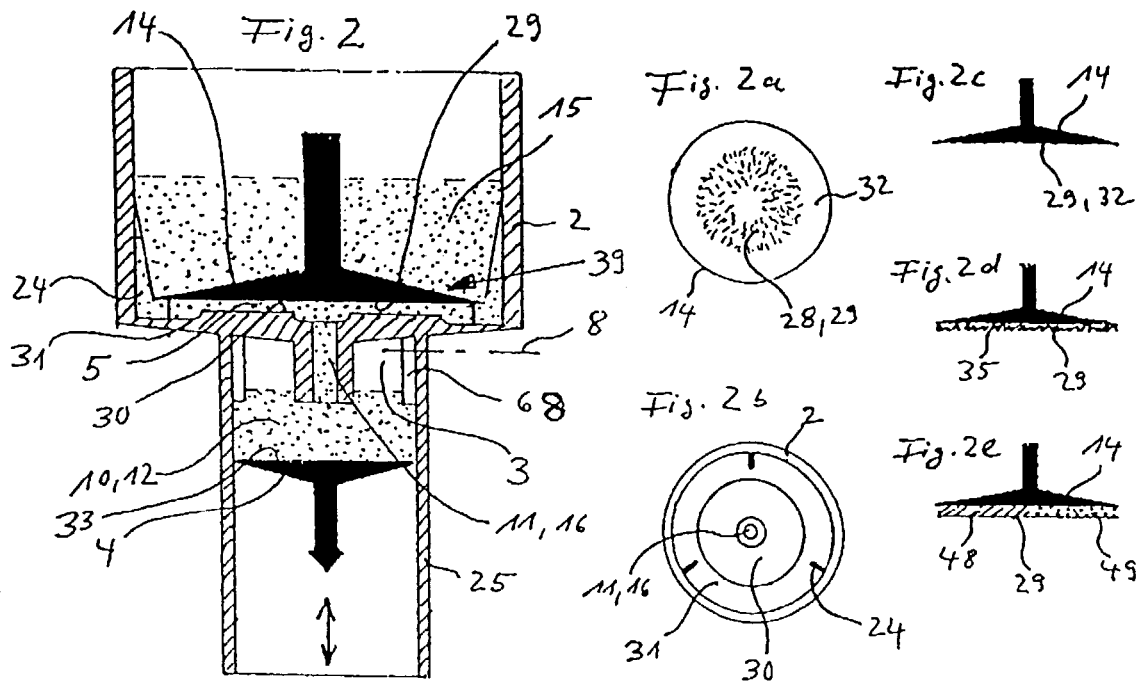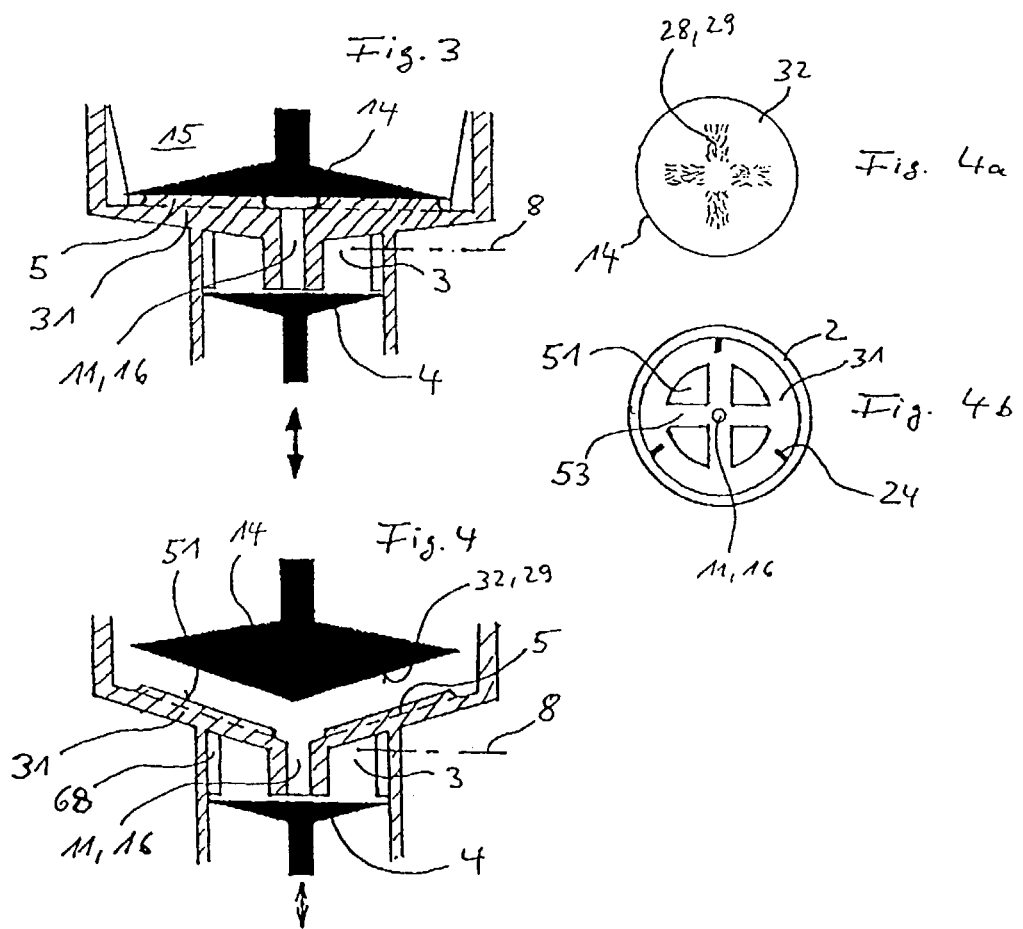

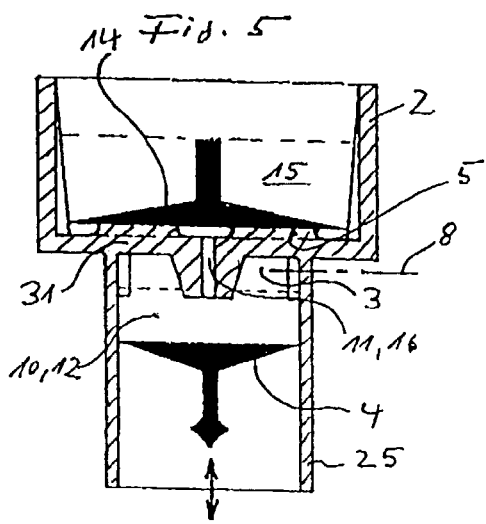
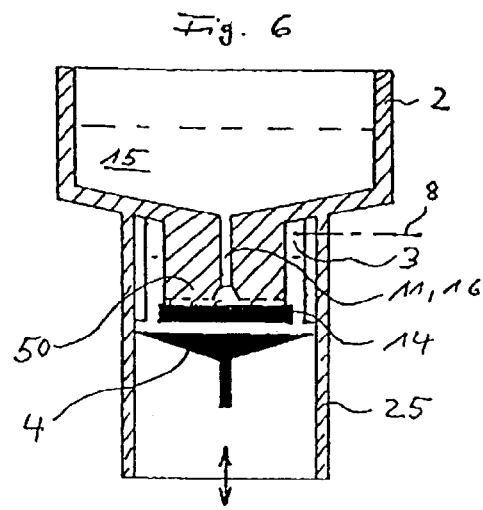
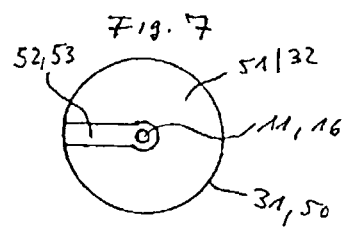
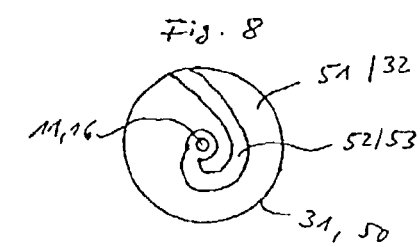
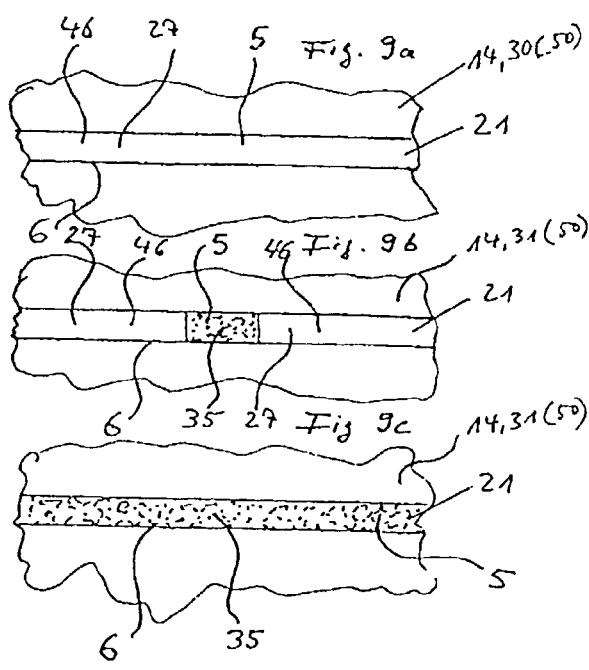
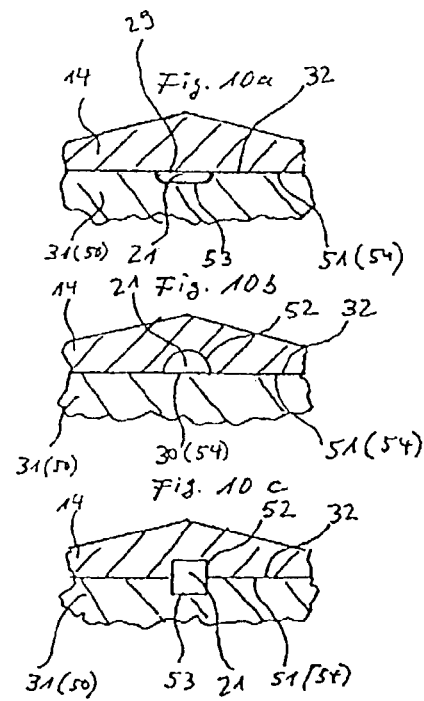

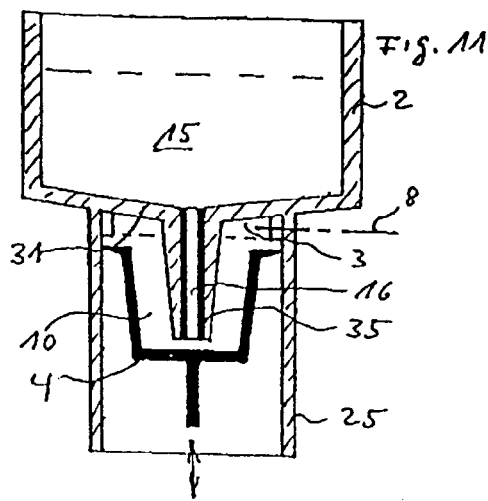
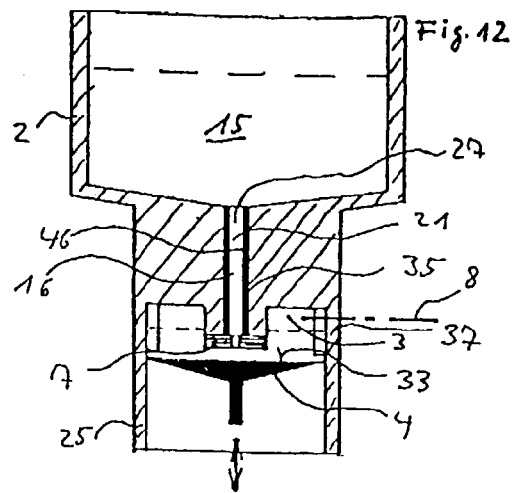
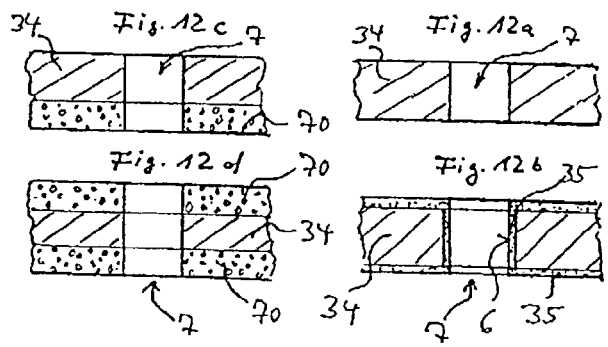
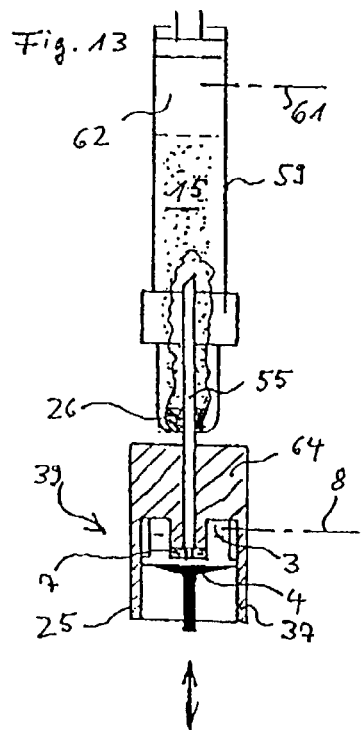
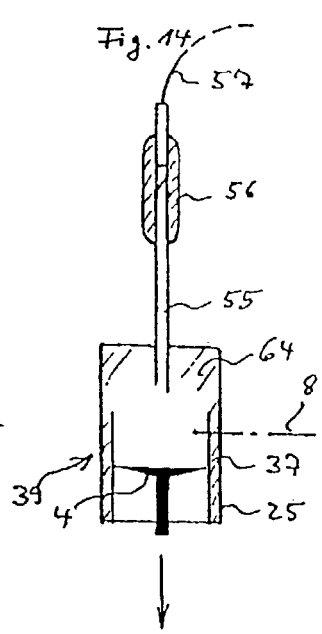
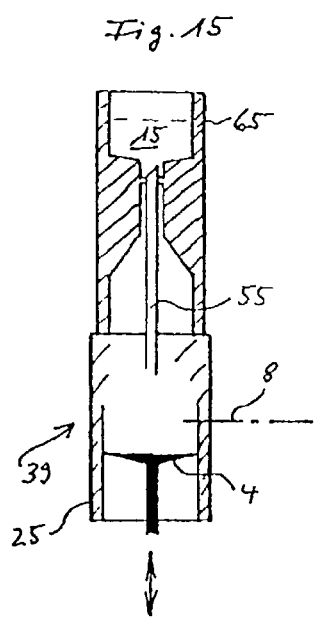

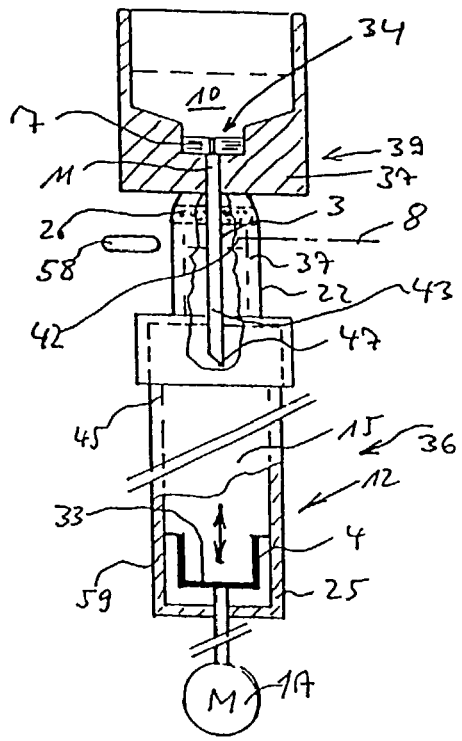
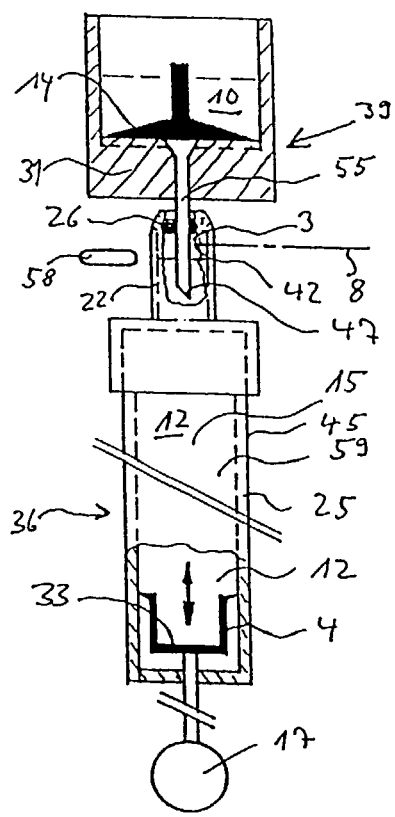

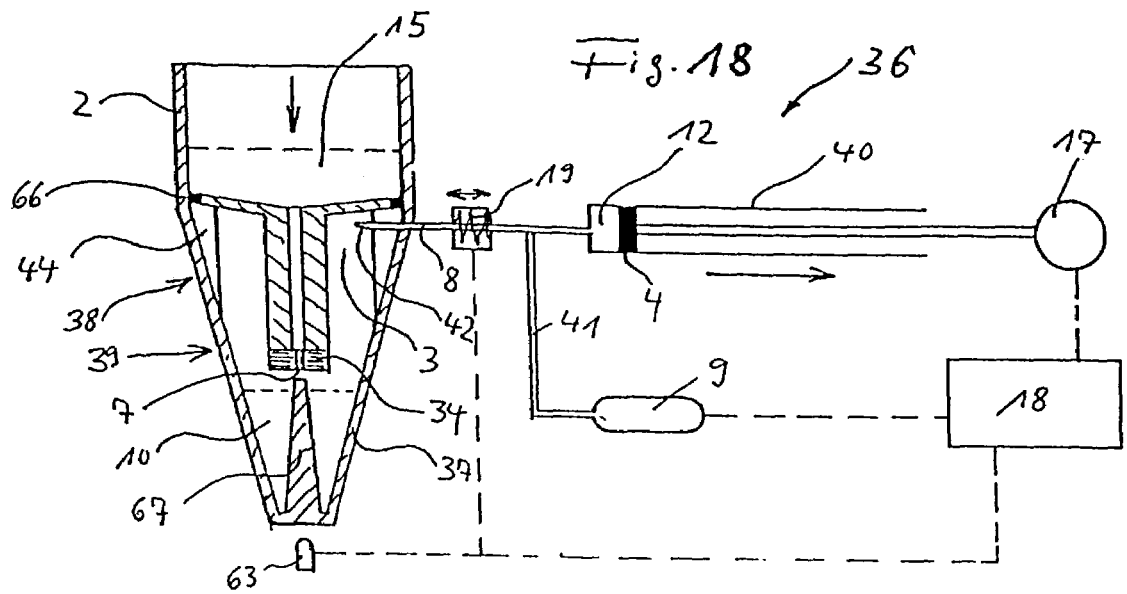
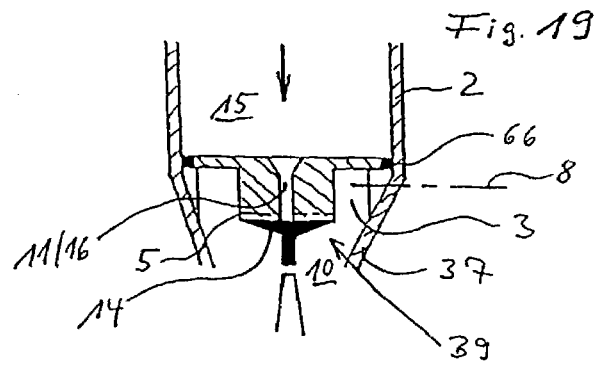
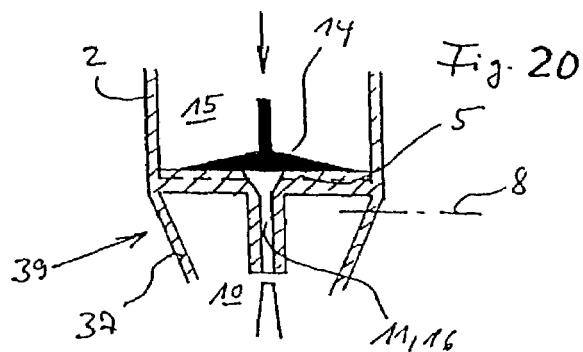
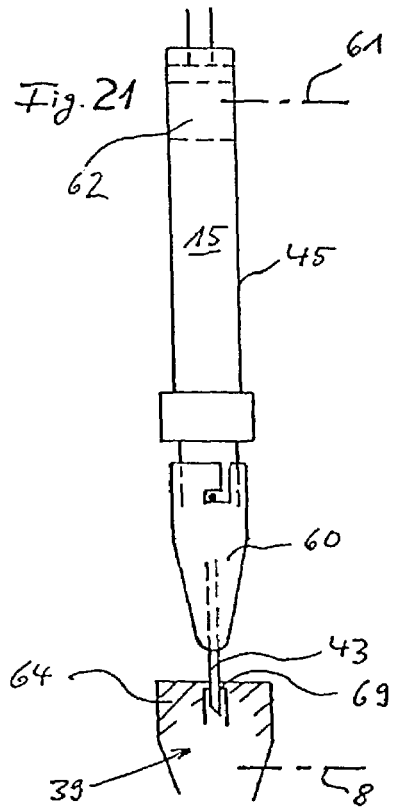

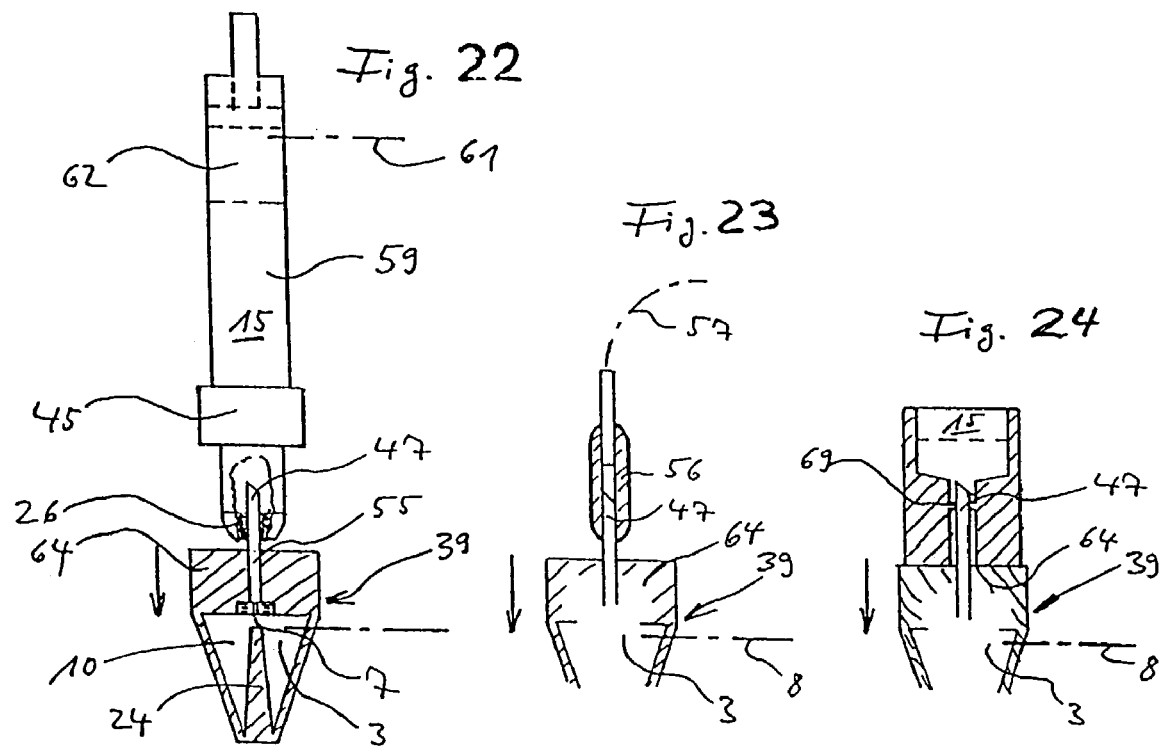
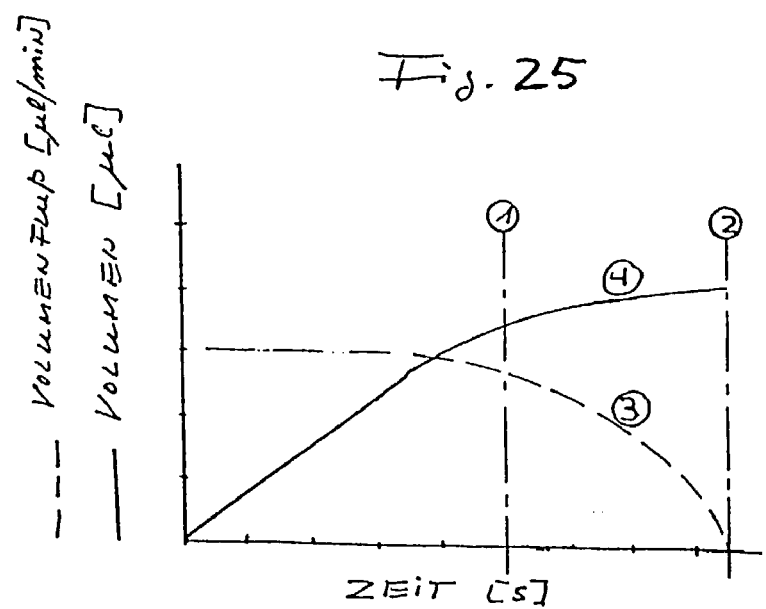

DEVICE AND METHOD FOR DETECTING THE COAGULATION FUNCTIONS OF GLOBAL, ESPECIALLY PRIMARY HEMOSTASIS

The invention relates to a device according to the preamble of claim 1 and to a method according to the preamble of claim 58.

PRIOR ART

Such a method and such a device are known from German Patent Application 196 17 407 A1, in which a volumetric flow of blood to be examined is transported from a storage vessel through a flow path, designed as an aperture, of a reaction device by means of a piston-cylinder system. The aperture becomes increasing blocked by aggregation and/or coagulation of blood components, particularly thrombocytes. The resulting pressure drop at the outlet side of the aperture is detected and measured in a pressure gauge chamber free of blood to be examined, via a supply line to a pressure sensor. The pressure gauge chamber is situated below the piston surface of the vertically upwardly moved piston adjoining the working chamber of the piston-cylinder system. The blood to be examined is thus upwardly conveyed from a storage chamber located below the aperture. The pressure gauge chamber is situated between the surface of the blood conveyed through the aperture and the underside of the piston. The pressure in the pressure gauge chamber is sampled and measured via the supply line which leads through the piston and which is connected to the pressure sensor.

In addition, a method and a device are known from European Patent Application 0 635 720 A1 in which the deposition or aggregation of thrombocytes is initiated under specified flow conditions. As the result of rotational movement with respect to a surface which the blood to be examined undergoes, shear forces appear on the surface. Thrombocytes deposit on the base of the container in which the blood to be examined is situated. The deposited thrombocytes are then evaluated by electron microscope scanning, optical image analysis, or the like.

In addition, it is known from European Patent 0 138 190 B1 that in a membrane opening through which a blood sample is transported, aggregation of thrombocytes can be initiated by shear forces in the opening (aperture). To measure the aggregation of the thrombocytes, the blood sample above the measurement aperture is subjected to pressure, and the time in which a specified reduction in the measurement aperture appears as the result of the aggregation of thrombocytes is measured.

In addition, a device is known from an article by Hubert Poliwoda et al., "Das Thrombometer: Seine Bedeutung als Globaltest zur Beurteilung der Thrombozytenfunktion" (The Thrombometer: Its Importance as a Global Test for the Evaluation of the Thrombocyte Function) (Klin. Lab. 6/95, pp. 457–464), by which the reaction of thrombocytes can be examined without unphysiological, mechanical, or chemical effects. To this end, whole blood is withdrawn from the vein of a patient using a cannula connected to the reaction device. The reaction device includes a collagen plate having a precisely bored opening with a diameter of 0.5 mm. The withdrawn blood flows through this opening with a velocity of 8 cm/s, each thrombocyte passing through the opening in the collagen in approximately 50 ms. A constant flow rate is forcibly maintained using a mechanically operated pump connected to the reaction device. The blood is aspirated at a velocity of 0.94 mL/min. The thrombocytes are detained as they pass the collagen opening, thereby increasingly closing the borehole in the channel of the reaction device. The time in which the suction pressure rises from 50 to 150 mbar is determined. In addition, a device may be placed between the cannula and the reaction device which continuously supplies the solution of a substance whose effect on the thrombocyte function on collagen may be tested. The pressure is measured in a suction tube filled with 0.9% NaCl solution.

A measuring device is known from U.S. Pat. No. 5,662,107 by which thrombus formation is measured in vitro under simulated in vivo conditions. To this end, blood is pumped at a constant flow rate through a channel which is made of a material promoting blood thrombosis or which is coated with such a material. The pressure is measured upstream and downstream from the thrombus-forming unit, and the difference in pressure is evaluated as the tendency toward thrombus formation. This indicates the importance of the shear rate for the deposition of platelets and the activation of coagulation. Care must be taken, however, that as the deposition of platelets increases, the shear rate increases unchecked when the flow rate is maintained.

OBJECT OF THE INVENTION

The object of the present invention is to provide a device and a method of the aforementioned type by which exact and reproducible measurement results are obtained at low measurement costs. For the device, this object is achieved by the characterizing features of claims 1, 2, and 3, and for the method, the object is achieved by the characterizing features of claim 58.

A very economical measuring device is thus provided, using a simple and low-maintenance technique, which can apply to the measuring inserts as well. The device offers the requisite features for the inexpensive production of a multichannel automatic device for use in large-scale laboratories as well as for a small device having one measuring channel, for example, or for use under severe conditions in the immediate vicinity of the patient (point of care). The method makes it possible to carry out the measurement run under controlled shear conditions in the changing reaction opening, and thus to form new, important diagnostic assays.

Whole blood or platelet-rich plasma can be used for the measurements of coagulation functions of global, in particular primary, hemostasis. Sodium citrate, hirudine, and other substances may be used as anticoagulants. To initiate coagulation, activators such as, for example, collagen, adenosine diphosphate, thrombin, and other substances listed below may be present on the boundary surfaces of the reaction openings, or they may be added to the blood sample before or during the measurement.

According to the invention, the pressure gauge chamber is situated below the storage chamber, from which the blood to be examined is conveyed. The reaction device is situated between the storage chamber and the pressure gauge chamber. After the blood passes through the reaction device, which may be situated underneath, for example in the base region of the storage chamber, the blood to be examined is led through the central flow opening and past the pressure gauge chamber to a pressure-sealed blood collection chamber, where it collects during the measurement process. The pressure gauge chamber is situated above the surface of the blood collected in the pressure-sealed blood collection chamber. Preferably, a pressure which is proportional to or equal to the conveyor pressure prevails in the pressure gauge chamber. A piston-cylinder drive system is preferably used to generate the conveyor pressure. To this end, the pressure gauge chamber may be situated in the working chamber of the piston-cylinder system, in which the pressure prevailing for the blood to be conveyed through the reaction opening in the measuring device is the conveyor pressure. The pressure in the pressure gauge chamber then corresponds to the conveyor pressure. A piston surface, as a working surface, thereby forms the boundary of the working chamber. The pressure gauge chamber is thus formed by the cylinder of the piston-cylinder system and one or multiple spacing means, in particular by a portion of the reaction device. The piston-cylinder system is preferably situated below a storage vessel in which the storage chamber is provided for the blood to be examined. The piston-cylinder system together with the expanding cylinder interior (working chamber) may form the blood collection chamber. However, as discussed below, the device which supplies the conveyor pressure, such as the piston-cylinder system, for example, may also be situated outside the blood collection chamber.

To sample the pressure prevailing in the pressure gauge chamber, a pressure sensor which supplies corresponding signals may be arranged in the pressure gauge chamber. Preferably, a pressure line such as a hollow needle is used which is guided through the wall of the pressure gauge chamber in a pressure-sealed manner and which is connected to a pressure gauge, such as a pressure sensor, outside the pressure gauge chamber. The hollow needle preferably has a tip in the form of an injection cannula on its end which is guided through the wall of the pressure gauge chamber. However, it is also possible to connect the pressure line, which is designed as a gas pressure line, to the pressure gauge chamber by using an integrally molded connector or other means. The wall enclosing the pressure gauge chamber is preferably made of plastic so that this wall can be penetrated by the needle in order to insert the end of the needle into the pressure gauge chamber in a pressure-sealed manner. Preferably, an electrically actuated valve is situated in a branch of the gas pressure line by which air can be transported away by the movement of the conveyor piston in the measuring cylinder, for example, in order to reduce air pockets in the pressure gauge chamber.

The supply vessel and the cylinder of the piston-cylinder system may be produced as a single piece. The reaction device by which the blood is led through the central flow opening and past the pressure gauge chamber is situated in the region of the base of the supply vessel.

In the measurement systems, the piston-cylinder system situated underneath may also be advantageously formed using a blood withdrawal syringe containing anticoagulated blood withdrawn from patients, the piston of which is connectable to drive 17 via a coupling. A hollow needle attached in a pressure-sealed manner at its one end in the central flow opening penetrates the sealing insert in the upwardly pointing syringe adapter, thus connecting the blood collection chamber (or storage chamber) to the storage chamber (or blood collection chamber) of the blood withdrawal syringe via the reaction device. In this embodiment, the blood storage chamber is formed in the working chamber of the cylinder of the withdrawal syringe. The flow opening in the hollow needle may be designed as a feed opening which preferably acts as a shear opening.

Preferably, before the measurement is begun the piston is moved upward in the syringe cylinder in the direction toward the reaction device, pushing the blood column formed by the inner wall of the cylinder upward with its working surface, with bleeder valve 20 open, until the upper blood level is detected at a precisely defined position by a level sensor which then signals the reference position to the control unit, whereupon the measurement can begin. The reference position defines the volume of the air pocket which forms the blood-free pressure gauge chamber and which is bounded by the outside of the hollow needle, the blood level, the inner wall of the syringe adapter, and the underside of sealing insert 26. This type of design is particularly suited for use in the immediate vicinity of the patient (point of care), because the complicated pipetting of the blood sample is omitted.

In the exemplary embodiments in which the conveyor device is situated outside the blood collection chamber, a pressure line, particularly a gas pressure line, which conducts the conveyor pressure is provided which is led in a pressure-sealed manner from the outside through a container wall of the pressure-sealed collection chamber, into the blood-free pressure gauge chamber. The container wall preferably is made of plastic, particularly polyethylene, or another material which during insertion makes pressure-sealed contact with the outside of the pressure line. For this purpose, the pressure line is preferably designed as a hollow needle (cannula) having a tapering needle end. The tapering needle end is pushed through the container wall into the pressure gauge chamber. The conveyor device may be designed in a known manner as a suction/pressure pump, piston-cylinder system, or the like, which in conjunction with the drive generates the conveyor pressure in the pressure line.

Preferably, the pressure line led through the container wall of the storage chamber or the collection chamber conducts the conveyor pressure as well as the pressure to be measured. To this end, the pressure line is connected outside the container wall to a pressure gauge, in particular a pressure sensor, via a branched pressure gauge line. The conveyor pressure corresponds to the pressure to be measured which prevails in the blood-free pressure gauge chamber.

The reaction device is preferably situated above the collection chamber, in a common housing with the collection chamber. In addition, the storage chamber above the reaction device may likewise be situated in the common housing. To this end, the storage chamber and at least portions of the reaction device as well as the collection chamber may be constructed in one piece to form the common housing. However, the separate reaction device may also be designed to be insertable into the common housing in a liquid-sealed manner.

The storage chamber may also be formed by the interior of the cylinder of a blood withdrawal syringe, the cylinder interior being connectable to the reaction device via a hollow needle. The hollow needle may be designed as a cannula in the blood withdrawal syringe which includes the storage chamber, which with its needle tip may be guided in a pressure-sealed manner from the outside to the reaction site of the reaction device. For this purpose, the base material of the reaction device may be designed in such a way that after being punctured by the hollow needle it makes self-sealing contact with the outside of the hollow needle. However, the hollow needle which leads to the reaction site of the reaction device may also be attached in a pressure-sealed manner to the reaction device and pushed with its free needle end through a sealing wall of the top-mountable storage chamber, such as the cylinder interior of a syringe. The sealing wall of the storage chamber is likewise made of a material, as previously described, which makes pressure-sealed contact with the hollow needle. The hollow needle preferably forms the feed opening for the blood from the storage chamber to the reaction opening, and may also preferably act as the shear opening. This type of design is particularly suited for use in the immediate vicinity of the patient (POC or point of care), because the complicated pipetting of the blood sample is omitted.

Various embodiments may be used for the reaction device. Preferably, an embodiment is used for detecting the coagulation properties of the global, in particular also the primary, hemostasis, in which the blood to be examined may be conveyed to the blood collection chamber by a conveyor device, in particular a piston-cylinder system which can be driven by a drive device from a storage chamber, via one or multiple reaction openings in the reaction device which may also simultaneously act as shear openings, to the blood collection chamber. Feed openings which may simultaneously act as shear openings may be situated upstream or downstream from the reaction opening(s), the surfaces of the shear openings being hydrophobic to avoid deposition of blood components at that location. The boundary areas of the reaction openings may also have a hydrophobic design or be provided with a roughness sample. The boundary surfaces or partial surfaces of one or multiple reaction openings or reaction sites on which blood components may optionally deposit or react under the effect of shear forces may be made of, for example, hydrophilic or optionally also hydrophobic plastic, glass, or porous or nonporous bioactive films/membranes, or collagen membranes, or porous membranes (cellulose acetate, for example), or may be coated with these materials, and additionally or as needed may have a reactive design for various investigations of the coagulation or platelet reaction by being bioactively coated, impregnated, or covered with, for example, thrombin or batroxobin, an extracellular matrix (ECM), collagen (also natural recombinant collagen or purified collagen subtypes), synthetic peptides having collagen-like amino acid sequences, or laminin or fibronectin, preferably thrombospondin, erythrocytes and/or leucocytes, preferably of blood type O or containing von Willebrand factor, or a mixture of collagen (as above) or synthetic peptides with substances such as adenosine diphosphate (ADP), adrenalin, fibronectin, thrombospondin, and/or other agents which induce the coagulation reaction (European Patent Application 0 316 599 A2, European Patent 0 111 942, U.S. Pat. No. 5,854,067, and U.S. Pat. No. 6,662,107).

In a blood vessel, the blood flow rate is inversely proportional to the radius of the blood vessel, and is lower at the vessel wall than in the center of the vessel. The difference in velocity between adjoining liquid layers flowing in parallel past one another produces a shear effect between these layers. This effect is greatest at the vessel wall, and diminishes toward the center of the vessel. The localized shear rate corresponding to the velocity gradients between two adjoining liquid layers flowing past one another affects the shear stress and is directly proportional to the velocity gradient. Correspondingly, various shear rates prevail at the surface of the vessel walls in different types of vessels. Physiological shear rates in large veins are <100 $s^{-1}$. For arteries, the wall shear rates vary between 100 and 1000 $s^{-1}$, depending on the diameter of the arteries, and in arterioles the shear rates reach approximately 1500 $s^{-1}$. In the coronary arteries the average shear rate is approximately 650 $s^{-1}$. Extremely high shear rates of approximately 3000 $s^{-1}$ to a maximum of 40,000 $s^{-1}$ exist in vessels constricted by atherosclerosis. Depending on the magnitude of the shear stress, in certain types of cells, particularly thrombocytes, the external shapes and reactivities as well as the binding behavior of the membrane and plasma proteins are altered. It is known that as the shear rate rises, normal thrombocytes, in particular those which are activated, increasingly adhere to collagen surfaces, for example, and then aggregate (atherosclerosis). In contrast, platelets whose function is inhibited by the effect of ASA (acetylsalicylic acid), for example, or by von Willebrand disease, adhere increasing less to collagen surfaces, for example, as the shear rate rises, and therefore aggregate (hemorrhage diathesis). This knowledge may be put to use according to the invention for the sensitive diagnosis of platelet functions of the primary hemostasis by moving a volumetric flow of blood in a controlled manner so that, using an aperture or reaction opening coated with collagen, for example, a predetermined, in particular constant, shear rate is maintained in the aperture or reaction opening which is growing smaller or closing due to the deposition and aggregation of thrombocytes. The volumetric flow of the blood to be examined which passes through the aperture/reaction opening may also be adjusted as a function of any desired predetermined shear rate or shear force characteristic curve.

The conveyor flow created by the regulated motion of the piston in the piston-cylinder system generates a conveyor pressure which, corresponding to the flow resistance, builds up in the reaction opening(s). The bloodstream creates shear or flow conditions in the reaction opening(s) by whose action thrombocytes may adhere and aggregate, corresponding to their functionality, at the boundary surfaces in the reaction openings(s) which are designed to be bioactive or capable of deposition. The thrombocytes may thereby reduce the open cross section of the reaction opening or may completely close this reaction opening by forming a thrombus, or, through the influence of the reactively designed boundary surface(s) of the reaction opening(s) or through the influence of supplied activators, result in a change in the blood flowability due to the onset of global blood coagulation, in particular by an alteration in the physical structure of polymerized fibrin and cellular components (platelets, erythrocytes, leucocytes) or by an increase in the force exerted on the fibrin network by activated thrombocytes. This generates a variable pressure in the conveyance path of the blood to be examined which is transported through the reaction device, this pressure acting in the pressure gauge chamber and being applied upstream or downstream from the reaction opening and being used to regulate the conveyed volumetric flow. According to the invention, the volumetric flow is adjusted in such a way that, depending on the particular measured pressure, the shear rate or shear force acting on the reaction site or in the reaction opening follows a predetermined characteristic curve which preferably corresponds to a constant shear rate/shear force, or which follows another predetermined curve for the shear rate or flow rate. The measurement and analysis results thus obtained correspond to the actual deposition and aggregation behavior of the thrombocytes, corresponding to the platelet reaction of the primary hemostasis or the coagulation behavior of the global hemostasis. For clinical analysis, the volumetric flow and/or the flow volume present which have flowed through the reaction device after a certain predetermined measuring time has elapsed may be determined, or, if the volumetric flow has reached a predetermined value or is approaching zero, the elapsed time and/or the flow volume are determined (German Patent Application 35 41 057 A1). In addition, for clinical analysis at a predetermined flow volume, the time elapsed and/or the volumetric flow present at the time are evaluated as platelet parameters. Furthermore, the measured pressure change and/or the volumetric flow achieved after a predetermined time, or the elapsed time when a predetermined pressure value and/or a volumetric flow is reached, may be used as measurement parameters for the global, in particular, hemostasis.

An additional measurement analysis is performed by providing after a precise predetermined measurement time an insert having at least one surface which is able to act as one or multiple boundary surfaces to form one or multiple reaction openings, it being possible to remove the insert from the measurement system. At the particular boundary surface, which optionally may be bioactive or capable of deposition, thrombocytes may have deposited and aggregated under the effect of shear forces or flow forces created according to a characteristic curve. The characteristic curve is preferably formed in such a way that it corresponds to a constant shear rate/shear force or flow rate. The extent and type of the platelet reaction on the boundary surface may be optically evaluated after fixing the platelet formation by an electronic microscope scanning system, for example, followed by computerized image analysis and display of the measurement parameters for making the clinical diagnosis. Other forms of optical evaluation may also be used (European Patent Application 0 635 720 A2).

Various embodiments may be used for the reaction device. Preferably, an embodiment is used in which the adhesion and aggregation of the blood components (thrombocytes) are induced under specified shear force conditions. A reaction opening (aperture) such as that in known devices may be used for measuring the platelet function of the primary hemostasis, for example in the form of an opening in a partition between the storage chamber and the pressure gauge chamber (European Patent Application 0 316 599 A2) or membrane (European Patent 0 138 190 B1 or European Patent 0 111 942). Preferably, one or multiple reaction openings (apertures) are used which are totally or partially enclosed by a hydrophilic material such as polystyrene, glass, or the like, or by a bioactive material, in particular collagen, or which are made of these materials (U.S. patent application Ser. No. 5,854,076 A; U.S. patent application Ser. No. 5,602,037; and U.S. application Ser. No. 5,662,107 A).

A very important factor for clinical acceptance of a method, in addition to supplying clinically relevant data, is the economical use of inexpensive, disposable measurement inserts and the ability to carry out the measurements using small blood samples. Thus, in the described reaction devices having a corresponding design, it is possible to use small quantities of blood for the measurement so that, under the described measurement conditions, blood is conveyed from the storage chamber, through the reaction device, into the collection chamber, and back, which may result in coagulation or platelet reactions of the global, in particular primary, hemostasis in the reaction opening(s) and in fact until the parameter-forming measurement limits (time, volume, volumetric flow, pressure, deposition formation for the optical evaluation, and so forth) of the particular measurement program have been reached, in order to then be able to provide diagnostic results, as previously described.

Methods for measuring the platelet reaction under shear conditions (European Patent Application 0 635 720 A2, for example) use a blood viscosity of 3000 µPa·s, for example, as the standard in calculating the shear rate. Under these conditions, all the measurements are then carried out without evaluating the existence of significant differences in the viscosity in different patients. After the viscosity, as a formula component, has exerted considerable influence on the magnitude of the shear rate, in reality very divergent shear rates are measured compared to the predetermined rates, which leads to erroneous measurement results. Advantageously, in the aforementioned measuring devices the blood viscosity can be specified in the initial phase by means of the precisely dimensioned geometry of the flow openings, the adjusted volumetric flow, and the resulting conveyor pressure, using a computerized control mechanism. Hence, the correct shear rate can be adjusted automatically, and the effect of the viscosity can be largely corrected as the measurement progresses.

EXAMPLES

The invention is described in more detail using exemplary embodiments, with reference to the figures:

FIG. 2 shows an enlarged illustration of an embodiment of a reaction device for detecting the coagulation functions of the global, in particular the primary, hemostasis, which may be used in the exemplary embodiment shown in FIG. 1;

Figure 1:
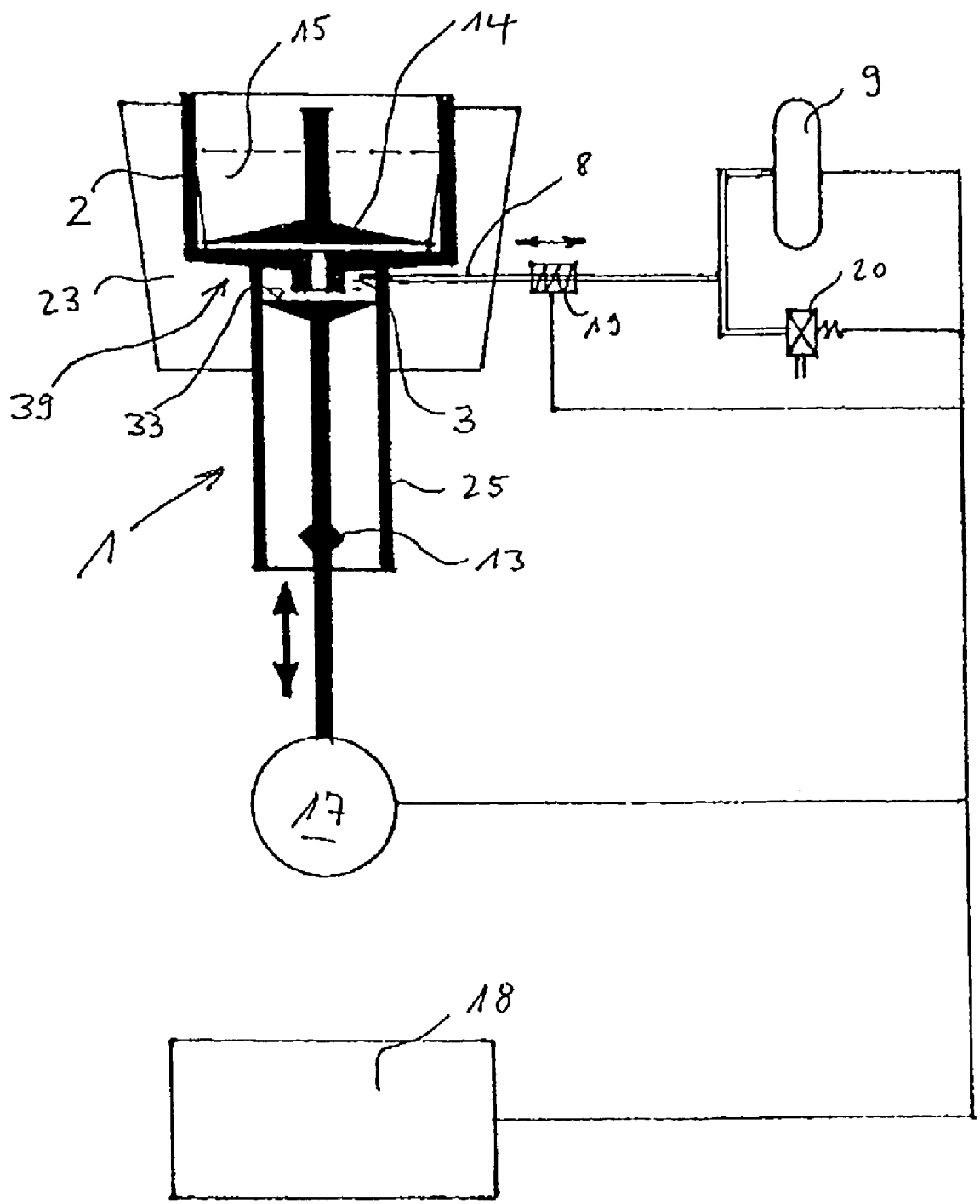
FIG. 1 shows an exemplary embodiment of a measurement system for detecting the coagulation functions of the global, in particular the primary, hemostasis in whole blood or platelet-rich plasma.
Figure 26:
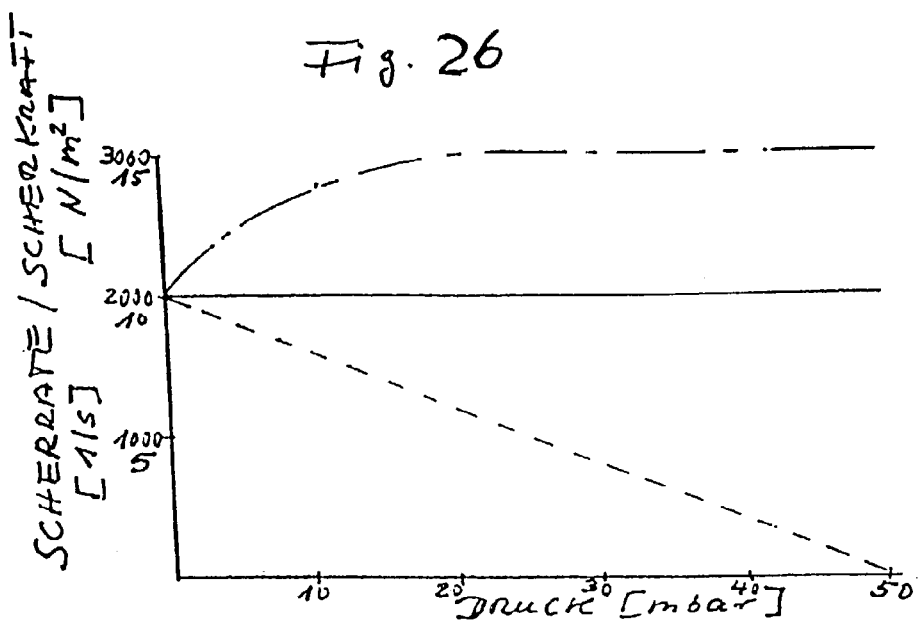
Figure 27:
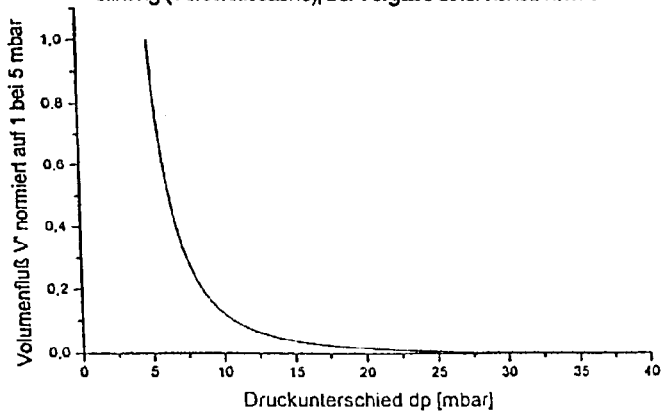
Figure 28:
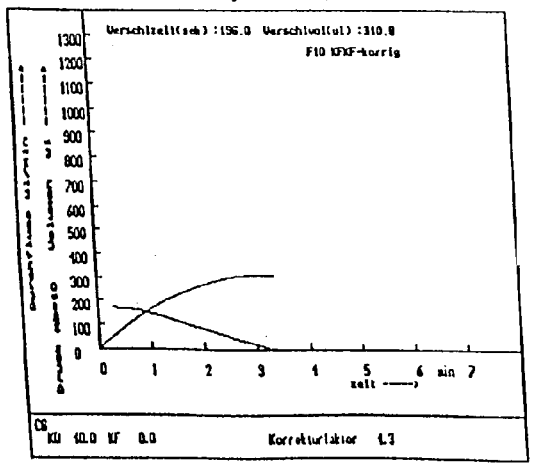

FIGS. 2a through 2e show embodiments of reaction sites which may be used in the reaction device shown in FIGS. 2 through 6, and FIGS. 17 and 19;

FIG. 3 shows a further embodiment of a reaction device for detecting the coagulation functions of the global, in particular the primary, hemostasis, which may be used in FIG. 1;

FIG. 4 shows a further embodiment of a reaction device which may be used in the device according to FIG. 1, and which corresponds to FIGS. 2 and 3 with respect to applicability;

FIGS. 4a and 4b show an embodiment of a reaction site which may be used in the reaction devices shown in FIGS. 3 and 4;

FIG. 5 shows a further exemplary embodiment of a reaction device which may be used in the device according to FIG. 1;

FIG. 6 shows a further exemplary embodiment of a reaction device which may be used in the arrangement according to FIG. 1;

FIG. 7 shows an embodiment of a reaction site impression in the vessel base/intermediate base of the vessel and/or an insert for forming flow openings which can be used in the exemplary embodiments shown in FIGS. 3 and 4; 5; 6; 17; and 19;

FIG. 8 shows an embodiment of a reaction site impression in the base/intermediate base of the vessel and/or an insert for forming flow openings which can be used in the exemplary embodiments of FIGS. 3 and 4; 5; 6; 17; and 19;

FIGS. 9a through 9c show embodiments of flow openings in reaction sites which may be used in the devices according to FIGS. 3 and 4; 5; 6; 11; 17; and 19;

FIGS. 10a through 10c show embodiments of flow openings in reaction sites which may be used in the devices according to FIGS. 3 and 4; 5; 6; 17; and 19;

FIG. 11 shows a further exemplary embodiment of a reaction device for detecting the coagulation functions of the global, in particular the primary, hemostasis, which may be used in the device according to FIG. 1;

FIG. 12 shows a further exemplary embodiment of a reaction device which may be used in the device according to FIG. 1;

FIGS. 12a through 12d show embodiments of reaction sites, in particular reaction openings, which may be used in the reaction device according to FIGS. 12; 13; 16; 18; and 22;

FIGS. 13 through 24 show further exemplary embodiments of measurement systems for examining blood, in particular for detecting the platelet function of the primary hemostasis;

FIG. 25 shows graphical illustrations of measurement results obtained using the exemplary embodiments of the measurement systems;

FIG. 26 shows graphical illustrations of various possible shear force/shear rate characteristic curves;

FIG. 27 shows a graphical illustration of a characteristic curve for regulating the volumetric flow depending on the pressure rise in a reaction opening, at a constant shear rate;

FIG. 28 shows measurement results for hemostasis functions; and

Figure 29:
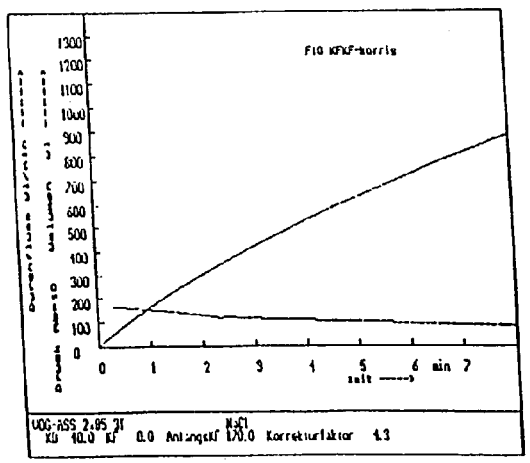

FIG. 29 shows measurement results for hemostasis functions.

In the device illustrated in FIG. 1, a storage chamber 15 for the blood to be examined is provided in a storage vessel 2. For the testing to detect the platelet function of the primary hemostasis and/or the functional properties of the global hemostasis, for example, the blood is transported from storage chamber 15 through a reaction device 39. Reaction device 39 has a reaction site, such as a reaction opening 5 or a reaction channel, for example, for which various embodiments may be provided. These embodiments are described in more detail below.

The particular reaction site (reaction opening) of reaction device 39 may be designed in such a way that blood components, in particular thrombocytes, adhere and aggregate there, thereby partially or totally clogging the reaction opening. The cross section of the flow provided in the reaction opening is thereby narrowed, resulting in increased flow resistance. A conveyor pressure corresponding to the pressure difference between a pressure, in particular suction pressure, generated by a conveyor device, and the external pressure (atmospheric pressure) acts on the blood to be examined which is present in storage chamber 15. This conveyor pressure is altered during the cross-sectional narrowing of the reaction opening as a result of the possible deposition and aggregation of thrombocytes, or by a reduction in the flowability of the blood caused by the onset of global, in particular primary, blood coagulation, and thus, increased flow resistance.

In the exemplary embodiments illustrated in the figures, a piston-cylinder system 1 is used to generate the conveyor pressure which acts in a working chamber 12 on one side of reaction device 39. This system comprises a cylinder 25 (measuring cylinder) in which a piston 4 is displaceably guided in the axial direction. A motor 17 is provided as the piston drive, which may be designed as a stepping motor. Motor 17 may be connected to piston 4 via a coupling 13. Coupling 13 is detachable, so that piston-cylinder system 1 can be separated from motor 17. In the exemplary embodiment illustrated, a pressure gauge chamber 3 is situated below storage chamber 15. Pressure gauge chamber 3 is located inside a pressure-sealed space into which the blood to be examined enters after passing through reaction device 39. In the exemplary embodiment illustrated, this pressure-sealed space is situated in working chamber 12 of piston-cylinder system 1. The blood which has passed through reaction opening 5 and central flow opening 11 of reaction device 39 collects on a working surface 33, which in the exemplary embodiments illustrated in FIGS. 1 through 17 is directed upward. Piston 4 is sealed with respect to the inner wall of cylinder 25 in such a way that the quantity of blood being collected can be used as a measured variable for the flow volume. A liquid meniscus which forms on the cylinder wall creates an additional gas-tight seal. Cylinder 25 may therefore be used at the same time as a measuring cylinder, since the movement of piston 4 by means of drive 17 may be regulated by control unit 18, thus enabling the volumetric flow and the flow volume through the reaction opening to be accurately detected as a measured variable.

Pressure gauge chamber 3 is situated above the surface of the blood present in cylinder 25 which has passed through reaction device 39. Pressure gauge chamber 3 is free of the blood to be examined. A pressure line 8 designed as a hollow needle projects into pressure gauge chamber 3. Hollow needle 8 may have a tip, which is pushed through the plastic material of cylinder 25. To this end, a lifting magnet 19 may be used to push hollow needle 8 through the wall of cylinder 25. This ensures a pressure-sealed penetration of hollow needle 8 through the cylinder wall. A pressure gauge (pressure sensor) 9 is connected to the hollow needle or pressure line 8. Pressure line 8 may also be joined in a pressure-sealed manner to pressure chamber 8 in other ways, via a connector, for example. Pressure gauge 9 generates measurement signals which correspond to the pressure in pressure gauge chamber 3. Instead of the arrangement illustrated for detecting and measuring the pressure, a pressure sensor may be installed in pressure gauge chamber 3 which generates corresponding signals which may be relayed wirelessly or via electrical connecting wires. Pressure gauge 9 is connected to a control unit 18. Control unit 18 controls the drive of motor 17, and thus the drive of piston 4, depending on the measured pressure in pressure gauge chamber 3. During the entire measuring process, piston 4 may optionally be moved in only one direction by the motor drive, specifically, from the upper position shown in FIG. 1 to a lower position. However, it is also possible, up to the end of a measurement, to effect a pulsating back and forth motion of the piston under predetermined measurement conditions, using motor 17 which is regulated by control unit 18. In this manner the blood is pulsatingly moved back and forth through reaction device 39 under predetermined shear conditions in the reaction opening(s) or shear opening(s). Hollow needle 8 may also be connected to bleeder valve 20, making it possible to optionally alter air pocket 62 in pressure gauge chamber 3 by the movement of piston 4.

Using a stop 68, it is possible to bring piston 4, which with its working surface 33 forms the lower boundary of a pressure-sealed blood collection chamber 10 for collecting the blood which has passed through reaction device 39, into a reference position by moving working surface 33 against this stop before the measurement is begun. As shown by the exemplary embodiments illustrated in FIGS. 2 through 12, storage vessel 2 and cylinder 25 are preferably constructed as one piece.

Storage vessel 2 and cylinder 25 may be enclosed by a heating sleeve 23 whose temperature can be regulated.

The figures illustrate various exemplary embodiments of the measurement system, and in particular, various embodiments of reaction devices 39 which may be used in the measurement system shown in FIG. 1.

In the exemplary embodiments illustrated in FIGS. 2 through 4, reaction openings 5 are designed in such a way that deposition of the blood components, in particular thrombocytes, is initiated on the boundary surface 29 of insert 14 by the action of regulated shear forces. After the measurement process has ended, insert 14 may be removed from storage vessel 2 and the deposited platelet formation 28 examined by optical, electron microscope, chemical, or physical means while forming clinical diagnostic measurement parameters.

In the exemplary embodiment shown in FIG. 2, reaction device 39 has a reaction site or reaction opening 5 which is formed by two oppositely facing boundary surfaces 29 and 30. Boundary surface 29, which preferably has a flat design, is situated on an insert 14 in the form of a plunger. Boundary surface 30 is situated on vessel base 31 of storage vessel 2. The two boundary surfaces 29 and 30 may run parallel or nonparallel with respect to one another, the increase in the distance between the outside and the inside being negligible. The distance between the two boundary surfaces 29 and 30 defines the height of reaction opening 5. In the exemplary embodiment illustrated, this reaction opening extends essentially horizontally, that is, perpendicular to the direction of motion of piston 4. The conveyor pressure in working chamber 12 generated by piston-cylinder system 1 situated underneath acts via a central opening 11 and reaction opening 5 in storage chamber 15 of storage vessel 2. Central opening 11 may also be formed by the interior of a tube 16 which can be inserted into central flow opening 11. Central flow opening 11 or tube 16 may be used as the feed opening and/or the shear opening. The blood is transported from the outer edge of reaction opening 5 to central flow opening 11 or tube 16. In reaction opening 5, shear forces act on the blood components, thereby enabling the thrombocytes to deposit and aggregate preferably on the underside of insert 14, that is, on boundary surface 29. Or, this may result in a change in the flowability of the blood during blood coagulation (clot formation) of the global, in particular the primary, hemostasis, especially by back and forth pumping of the blood through the reaction opening. Since boundary surface 30 has hydrophobic properties, platelet reaction cannot occur there.

Plunger-shaped insert 14 is properly positioned in the storage vessel by means of locking and spacing bars 24. The gap height of reaction opening 5 is fixed by the spacer function. Boundary surface 29 is designed as a reaction surface on the underside of insert 14, which optionally is removable from the measurement system by means of a gripping arrangement (not shown in greater detail). For this purpose, this boundary surface may be appropriately coated or designed, as shown in FIGS. 2c through 2e. For example, underside 32 of insert 14, which forms boundary surface 29, or the entire insert 14 may be made of a hydrophilic material, such as polystyrene or glass, on which platelets can adhere. For certain applications, underside 32 may be kept hydrophobic and/or be provided with a roughness sample. On lower surface 32 of insert 14 it is also possible to provide, as shown in FIG. 2d, a bioactive coating 35 in the form of an extracellular matrix (ECM), thrombin, batroxobin, collagen (also natural recombinant collagen or purified collagen subtypes), synthetic peptides containing collagen-like amino acid sequences, laminin, thrombospondin, fibronectin, blood cells, in particular erythrocytes or leucocytes, preferably of blood type O or containing von Willebrand factor, or a mixture of collagen (as above) or synthetic peptides, respectively, with substances such as adenosine diphosphate (ADP), adrenalin, thrombospondin, or fibronectin, or other bioactive substances as described in U.S. patent application Ser. No. 5,854,076A or U.S. patent application Ser. No. 5,662,107A, for example, in order to form such a bioactive boundary surface 29 for reaction opening 5. In addition, boundary surface 29 may be designed in such a way that the surface of the insert is totally or partially covered with a nonporous coating 48 and/or a porous coating 49 in the form of a film or membrane (cellulose acetate), as shown in FIG. 2e. This coating may be covered or impregnated with the bioactive substances listed above. The bioactive film or membrane may also be made of collagen. As indicated in FIG. 2e, the coating may have a varied design. A plurality of measurement results may then be simultaneously obtained, if desired. The varied covering/coating may be produced in sections or in halves. FIG. 2a shows boundary surface 29 with deposited thrombocytes after a measurement has been carried out. FIG. 2b shows vessel base 31 in a top view for clarification.

In FIGS. 3 and 4, the blood flowability may be altered during blood coagulation (global hemostasis) in the same manner as for FIG. 2; otherwise, the platelet reaction of the primary hemostasis should likewise preferably take place on boundary surface 29 of insert 14, as shown in FIG. 2, and both (29 and 14) may be designed according to the description for FIG. 2 (material and bioactive covering/coating). Insert 14 is likewise removable. The design shown in FIG. 4 differs from that in FIG. 3 solely by the fact that insert 14 along with surface 32, which forms boundary surface 29, has the shape of a flattened cone, and vessel base 31 has been adapted to the shape of support surface 51.

In the embodiments illustrated in FIGS. 3 and 4, cross-shaped impressions 53 are molded into vessel base 31 (FIG. 4b). These impressions 53 form indentations between support surfaces 51 on which insert 14, along with surface 32 forming boundary surface(s) 29 of reaction opening(s), rests with a friction fit. This results in reaction openings 5 which are arranged in a cross shape extending essentially radially and horizontally (FIG. 3), as well as inclined reaction openings 5 (exemplary embodiment shown in FIG. 4). This results in cross-shaped deposits 28 of thrombocytes on boundary surfaces 29, which may be formed by surface 32 of insert 14, as shown in FIG. 4a. The surfaces of vessel base 31, intermediate base 50, and all surfaces which are created there by impressions 53, 52 may optionally have a hydrophobic design to avoid undesired platelet deposits.

FIGS. 5 and 6, 17, and 19 show further exemplary embodiments of reaction devices 39 in which flow openings 21 are created by joining an insert 14 and its surface 32 to support surface 51 of vessel base 31 or intermediate base 50 and its support surface 54. These flow openings may form reaction openings 5 or feed openings 27 and shear openings 46.

Impressions 53 are preferably molded in vessel base 31 or intermediate base 50, as illustrated in FIGS. 4b, 7, and 8, for example. These impressions 53 form support surface 51 on which insert 14 is joined to its surface 32 with a friction fit. This surface 32 represents a boundary surface 29 of impression 53, by which a flow opening 21 could be formed, as shown in FIG. 10a. In this arrangement, surface 32 of insert 14 may also be designed in such a way that the surface represents a boundary surface 29, as described for FIGS. 2c through 2e, which along with impression 53 creates a flow opening which acts as a reaction opening 5 in which thrombocytes may optionally deposit and agglomerate.

In a similar manner as above, flow opening 21 may also be designed in such a way that an impression 52 is present only in insert 14, and the impression creates a support surface 32 there which is joined with a friction fit to support surface 51 of vessel base 31, or to support surface 54 of intermediate base 50, thereby forming a boundary surface 30 or 54, respectively, to form a flow opening 21 for impression 52 as shown in FIG. 10b. The boundary surfaces of flow opening 21 may then be designed according to FIGS. 9a, 9b, and 9c and their descriptions. In addition, impressions 52 may be freely chosen with respect to their number and shape, and may also correspond to those in intermediate base 31, according to FIGS. 4b, 7 and 8.

Furthermore, similar to the description above, mirror-image impressions 52 may be situated in insert 14 and impressions 53 may be situated in vessel base 31 or intermediate base 50, which then form mutual support surfaces 32 and 51 or 54, respectively. These mutual support surfaces are joined to one another with a friction fit so that impressions 52 and 53 overlap precisely to form a flow opening 21, as shown in FIG. 10c, for example. The boundary surfaces of flow opening 21 may then be designed according to FIGS. 9a, 9b, and 9c and their descriptions.

The cross sections of flow openings 21 in FIGS. 10a through 10c are shown as examples, and may have different shapes or may be exchanged with one another. On the other hand, the number, type, and shape of flow openings 21 may be differently chosen, as shown in FIGS. 4b, 7, 8, and 9a through 9c, depending on the requirements.

Flow openings 21, whose design has been described for the reaction devices shown in FIGS. 5 and 6, 17, and 19, may perform different functions as a result of the respective surface structure/coating created. In FIG. 9a, the section of a flow opening 21 shown is a feed opening 27, for example, and at the same, if desired, is a shear opening 46 when boundary surfaces 6 of opening 21 act hydrophobically. If, on the other hand, boundary surface 6 is kept hydrophilic, a reaction opening 5 is formed in which platelets may react. FIG. 9b shows that in flow opening 21 a predetermined area of boundary surface 6 is provided with a bioactive coating 35, thereby forming a reaction opening 5. The upstream and downstream areas represent boundary surfaces 6 which are kept hydrophobic and which therefore can simultaneously form feed openings 27 and shear openings 46. FIG. 9c shows a flow opening 21 whose boundary surface 6 has received a bioactive coating 35 along its entire length, thereby forming a reaction opening 5 on which platelets can react under the action of shear forces. Feed openings 27 and shear openings 46 may have a different cross section, similarly as for reaction opening 5, in the exemplary embodiments shown in the aforementioned figures. Bioactive coating 35 may be made of collagen (also natural recombinant collagen), synthetic peptides having collagen-like amino acid sequences, purified collagen subtypes, laminin, fibronectin, thrombospondin, and other erythrocytes, or may be made of a mixture of collagen (as above) or synthetic peptides with adenosine diphosphate (ADP), adrenalin, fibronectin, thrombospondin, or other substances which activate the platelets (U.S. patent application Ser. No. 5,854,067A and U.S. patent application Ser. No. 5,662,107A).

In the exemplary embodiments shown in FIGS. 2 through 6, 17, and 19, insert 14 and vessel base 31 are made predominantly of plastic. The cross section of insert 14 which forms surface 32, in addition to the shapes shown in FIGS. 2 through 4, may also have an arc-shaped or a downwardly tapering design, and vessel base 31 together with its boundary surface 30 or support surface 51 are then adapted to these shapes. Insert 14, as seen from above, may have a round shape, or also a triangular, oval, square, or polygonal shape, as may the receiving device in vessel base 31 in a corresponding manner. An insert receptacle may be molded on vessel base 31 and/or on the vessel wall of storage vessel 2 in the form of locking and spacing bars 24 into which insert 14 is introduced.

The embodiment shown in FIG. 5 corresponds for the most part to the embodiment arrangement shown in FIG. 3, except that in FIG. 5, insert 14 cannot be removed from the storage vessel. The embodiment possibilities of reaction device 39 correspond to FIGS. 4a and 4b, 7 and 8, 9a, b, and c, 10a, b, and c, and their previous descriptions. A tube 16 or hollow needle 55 made of steel, plastic, or glass may be inserted into central opening 11, the flow surfaces of the tube or hollow needle having a hydrophobic design so that shear effects (pre-shearing) can be created without producing platelet deposition there. In reaction openings 5 and 7 in reaction device 39, the action of these pre-shear forces results in platelet deposition. This is true for all the embodiments shown in FIGS. 2 through 24.

In the embodiment illustrated in FIG. 6, intermediate base 50 is formed on an extension of vessel base 31. Intermediate base 50 includes central opening 11 through which the blood to be examined is led from storage chamber 15 into reaction device 39. The blood flows from central opening 11, outwardly from the center to the edge of the reaction device. The embodiment possibilities of reaction device 39 likewise correspond to FIGS. 4a and 4b, 7 and 8, 9a, b, and c, 10a, b, and c, and their previous descriptions. A tube 16 may be inserted into central opening 11 of intermediate base 50, in which pre-shearing of the blood optionally takes place, corresponding to the description for FIG. 5. The same reaction device 39 is provided in FIG. 19.

The illustrated exemplary embodiments of the measurement system may have the following dimensions. The diameter and the height of storage vessel 2 may be approximately 10 to 20 mm. The height of measuring cylinder 25 may be approximately 20 to 50 mm. The diameter of measuring cylinder 25 may be approximately 8 to 15 mm. Flow opening 21 in central flow opening 11 may have a diameter of approximately 0.300 to 3 mm, and for tube 16, a diameter of approximately 0.100 to 2 mm. The length of central flow opening 11 and of tube 16 may each be 0 to approximately 35 mm. The volume present in pressure gauge chamber 3 may be approximately 10 to 50 µL, although in FIGS. 18 through 24 the volume is approximately 500 to 1000 µL.

In the exemplary embodiment illustrated in FIG. 11, tube 16 is situated in an extension which is integrally molded on vessel base 31. The tube may be made of plastic, glass, or steel. Flow opening 21 of tube 16 may be designed as a reaction opening 5 and lined with a bioactive coating 35 according to the description for FIG. 9c. Corresponding to FIG. 9b and its description, however, flow opening 21 may also be divided into a dimensioned section which forms reaction opening 5, and one or two remaining sectional portions which may form feed openings 27 or shear openings 46. The region representing reaction opening 5 may also be situated at the inlet, in the center, or at the outlet of tube 16.

The tube preferably is made of polystyrene or glass, boundary surface 6 of flow opening 21 then having a hydrophilic design (in which case the bioactive coating may be omitted), thereby forming reaction opening 5 according to FIG. 9a and its description. The diameter of flow opening 21 of tube 16 may be approximately 0.15 to 2 mm. The length may be approximately 10 to 30 mm. Optionally, tube 16 may be arranged in the extension so as to be removable, so that evaluation is possible outside the measurement system after the measurement has been completed. In the exemplary embodiment illustrated, piston 4 is cup-shaped on its upper end and encloses the downwardly directed extension, integrally molded on vessel base 31, in which tube 16 is situated. In this manner the smallest possible air pocket 62 can be formed in pressure gauge chamber 3.

In the embodiment shown in FIG. 12, a reaction opening 7 is provided on the lower end of tube 16 which runs in an extension of the vessel base. Flow opening 21 of tube 16 may act as a feed opening 27 and/or a shear opening 46. Reaction opening 7 may be designed in a manner known from European Patent 0 111 942 or European Patent Application 0 316 599 A1. Reaction opening 7 or partition 34 are preferably designed as illustrated in FIGS. 12a through 12d. In the embodiment shown in FIG. 12a, reaction opening 7 is situated in a partition 34 which is made of plastic, for example polystyrene, having hydrophilic surfaces, or which is made of a bioactive material, capable of depositing platelets, in the form of a bioactive film or a nonporous collagen membrane, for example. In the embodiment shown in FIG. 12b, partition 34 is made of a nonporous material provided with a bioactive coating 35, as described below, on one or both partition surfaces, or on both partition surfaces and/or on boundary surface 6 of reaction opening 7. In the embodiment illustrated, both partition surfaces of partition 34 and the boundary surface of the opening are provided with a bioactive coating 35. Bioactive coating 35/impregnation may be made of collagen (also natural recombinant collagen or purified collagen subtypes), synthetic peptides having collagen-like amino acid sequences, laminin, fibronectin, thrombospondin, or other substances, or bioactive substances (U.S. patent application Ser. No. 5,854,076A or U.S. patent application Ser. No. 5,662,107A) to which platelets adhere, or a mixture of collagen (as above) or synthetic peptides with adenosine diphosphate (ADP), adrenalin, fibronectin, laminin, thrombospondin, or other substances which activate the platelets. In the embodiments shown in FIGS. 12c and 12d with reaction opening 7, it is advantageous to coat one or both partition surfaces of nonporous partition 34 with a porous layer 70 or membrane (sandwich) made of cellulose acetate, for example, with corresponding coating/impregnation as described in FIG. 12b for nonporous partition 34. However, it is also possible to use only a porous material as partition 34 which is coated or impregnated in the same manner as for the aforementioned nonporous material shown in FIG. 12b (U.S. Pat. No. 5,854,076).

In the exemplary embodiment illustrated in FIG. 12, reaction opening 7 is situated at the lower end of tube 16, which may have a length of 0 to approximately 35 mm and a diameter of approximately 0.150 to 2 mm. Partition 34 having reaction opening 7 may also be provided approximately in the center of tube 16, in the direction of the longitudinal axis of the tube (not shown). In the absence of tube 16, partition 34 having reaction opening 7 may also be installed in a recess in vessel base 31. The diameter of the opening of reaction opening 7 may be approximately 0.100 to 0.500 mm. The wall thickness of the partition may be approximately 0.10 to 6 mm.

In the exemplary embodiment illustrated in FIG. 13, the storage chamber is situated in cylinder 59, preferably in a blood withdrawal syringe. Reaction device 39 is essentially designed as illustrated in FIG. 12, but may also have a design as illustrated and described for FIGS. 6 and 11. The blood to be examined which is present in storage chamber 15 of syringe cylinder 59 of withdrawal syringe 45 flows through a hollow needle 55 which is attached in a pressure-sealed manner in housing 64 and which with its upwardly pointing free needle end 47 is inserted through a sealing insert in syringe adapter 22 of syringe cylinder 59, through reaction device 39, and into blood collection chamber 10 situated underneath. To this end, as already described, piston 4 is moved downward along measuring cylinder 25 to carry out the measurement. Also in this embodiment, piston 4 in measuring cylinder 25 may optionally move the blood back and forth in reaction device 39 under the measurement conditions. Hollow needle 55 has a totally hydrophobic design on the surface, and may be made of steel, plastic, or glass. Its flow opening may act as a feed opening 27 and as a shear opening 46. This embodiment of hollow needle 55 may be used in the same way as shown in FIGS. 14 and 15, and 22 through 24.

Reaction opening 7 is preferably designed as described in FIGS. 12a and 12b. The pressure is measured in pressure gauge chamber 3 via pressure line 8, as explained in the previously described exemplary embodiments. Hollow needle 55 is firmly attached to a housing 64 in which reaction device 39 is accommodated. Ventilation/bleeding 61 is provided for an air pocket 62 situated above the blood sample present in storage chamber 15 so that no back pressure can develop in this space during the measurement movement of piston 4 in piston-cylinder system 1.

In the exemplary embodiment illustrated in FIG. 14, hollow needle 55 is likewise attached to housing 64 of reaction device 39. Reaction device 39 may also be designed in the same manner as for the exemplary embodiments shown in FIGS. 6 and 11 through 13. Hollow needle 55 is provided with a catheter 57 via a sealing collar 56 for the direct measurement of the patient's blood from the vein, for example.

In the exemplary embodiment illustrated in FIG. 15, storage chamber 15 for the blood to be examined is situated in a container 65 which may be mounted on hollow needle 55 which is fastened to housing 64. The tip of free needle end 47 is pushed into storage chamber 15 in the base region of container 65. The penetrated material in the base region of container 65 makes sealing contact with hollow needle 55, so that when piston 4 is moved the desired transport of the blood to be examined takes place through reaction device 39. In contrast to FIG. 13, this embodiment is suitable for measuring pipetted blood to which substances have been added, for example, or which has been otherwise manipulated, or for measuring when only a small quantity of blood (less than 500 µL, for example) is available for a control measurement. In this exemplary embodiment, reaction device 39 may likewise be designed as illustrated in FIGS. 6 and 11 through 14.

In the exemplary embodiment illustrated in FIG. 16, the piston-cylinder system of a specialized syringe (not shown) or a withdrawal syringe (disposable part) acts as a conveyor device to transport the blood to be examined from working chamber 12 of the conveyor device, which here is used as a storage chamber 15, via hollow needle 55 which is fastened in a pressure-sealed manner in central flow opening 11, and then through reaction device 39. In this arrangement, the upper vessel includes blood collection chamber 10. For this purpose, piston 4 present in syringe cylinder 59 is connected to drive 17 via a coupling, not illustrated in further detail. Using electric drive device 17 according to the measurement program regulated by control unit 18, piston 4 in syringe cylinder 59 may be moved upward in one direction for conveying the blood through reaction device 39. Piston 4 may also be moved back and forth so that the blood present in partition 34 flows through reaction opening 7 from alternating directions. The reaction opening may be designed according to FIGS. 12a and 12b and the description for FIG. 12. Partition 34 may be situated in a recess in vessel base 31 of upper vessel 2.

In the exemplary embodiment illustrated in FIG. 16, reaction devices 39 may also be used which correspond to the exemplary embodiments shown in FIGS. 2 through 5, 11, and 17 and the accompanying descriptions.

In order to connect reaction device 39 to the withdrawal syringe, whose working chamber 12 in this particular embodiment is at the same time storage chamber 15 and is filled with anticoagulated blood withdrawn from patients for carrying out the measurement process, the downwardly projecting free needle end 47 of hollow needle 55 is guided in a pressure-sealed manner through sealing insert 26 into a syringe adapter. The interior of syringe adapter 22 of withdrawal syringe 45 forms pressure chamber 3. The other end of hollow needle 55 is firmly connected to vessel base 31 in central flow opening 11. As already mentioned, withdrawal syringe 45 forms piston-cylinder system 1 whose piston 4 is connected to drive 17 via a coupling 13, not shown. Piston 4 is preferably moved upward in cylinder 25 in the direction toward reaction device 39, pushing the blood column formed by the inner wall of cylinder 25 upward with its working surface, with bleeder valve 20 open, until the upper blood level is detected at a precisely defined position by a level sensor 58 which then signals the reference position to control unit 18, whereupon the measurement can begin. The reference position defines the volume of air pocket 62 which forms blood-free pressure gauge chamber 3 and which is bounded by the outside of hollow needle 55, the blood level, the inner wall of syringe adapter 22, and the underside of sealing insert 26.

FIG. 17 shows an embodiment having a reaction part 39 which may correspond to those shown in FIGS. 2 through 5. Otherwise, the embodiment is identical to that described in FIG. 16.

In the exemplary embodiments illustrated in FIGS. 18 through 24, a conveyor device 36 for generating the conveyor pressure is situated outside common housing 38. The conveyor device comprises a piston-cylinder system having a cylinder 40 and piston 4. As described for the aforementioned exemplary embodiments, piston 4 is driven by an electrical drive device such as a stepping motor 17. Pressure line 8, which may be designed as a hollow needle, and whose tip is pushed through container wall 37 of blood collection chamber 10 by means of a drive 19 according to the description for FIG. 1, conducts the conveyor pressure generated in working chamber 12 of the piston-cylinder system. This pressure corresponds to the pressure to be measured in pressure gauge chamber 3. To this end, a pressure gauge line 41 is branched off from pressure line 8 and connected to pressure gauge line 9. In a manner similar to the exemplary embodiments already described, pressure gauge 9 (sensor) is connected to control unit 18 to which electrical drive unit 17 is joined. Blood collection chamber 10 is situated in common housing 38 below storage vessel 2. Reaction device 39 may be designed as shown in the exemplary embodiments illustrated in FIGS. 12 through 15. Another possibility is that reaction device 39, which is preferably designed as a separate insert, is inserted in common housing 38 of storage vessel 2 and in blood collection vessel 66 in such a way that it comes to rest on boundary bars 44. For this purpose, the outer ring of the portion of reaction device 39 which forms vessel base 31 is designed in such a way that the ring is able to act as a sealing element 66 for the inner wall of storage vessel 2. This embodiment may also optionally be used with other embodiments. A blood sensor 67 is situated in blood collection chamber 10 below reaction device 39. This sensor determines the first drops of blood passing through reaction device 39, and a converter 63 then sends a signal to control unit 18 indicating readiness to start the measurement.

However, the embodiments already described in FIGS. 2 through 17 may also be used for reaction devices 39.

A reaction device 39 is used in FIG. 19 as described in the exemplary embodiment shown in FIGS. 3 and 5.

A reaction device is used in FIG. 20 as described in the exemplary embodiment shown in FIGS. 3 and 5.

In the exemplary embodiment illustrated in FIG. 21, storage chamber 15 for the blood to be examined is situated in the cylinder of a withdrawal syringe 45 in a manner similar to the exemplary embodiment shown in FIGS. 13 and 22. Reaction device 39 is situated in housing 64 which, as shown in FIG. 18, has pressure-sealed blood collection chamber 10 in its lower portion. Piston-cylinder system 36, by which the measurement pressure is built up and which is used to convey the blood through reaction device 39, may be designed as illustrated in FIG. 18.

A hollow needle 43 connected to withdrawal syringe 45 via cannula adapter 60 may be pushed through a region of the wall of housing 64, as shown in FIG. 21. A pressure-sealed connection is established with reaction device 39 inside the housing. The measurement process for examining the blood, the combination with reaction devices 39 shown in the other figures, and the design of parts are achieved as explained for the aforementioned exemplary embodiments, particularly as in FIG. 13. Ventilation/bleeding 61 is provided for an air pocket 62 situated above the blood sample present in storage chamber 15, so that no back pressure can develop in this space during the measurement movement of piston 4 in piston-cylinder system 36.

Instead of the conveyor device in the form of piston-cylinder system 36 as shown in FIG. 18, a piston-cylinder system 1 may be used which is integrated into housing 64, as used in the exemplary embodiments of FIGS. 1 through 17. The possible reaction devices 39 may also be used as described and designated for FIGS. 13 and 22.

The exemplary embodiment illustrated in FIG. 22 is employed by using the external conveyor device in the form of a piston-cylinder system 36 corresponding to FIG. 18. Blood collection chamber 10 is situated in a container sealed at the bottom, also as in FIG. 18. Otherwise, this design is essentially identical to that shown in FIG. 13 and its description.

The measurement system illustrated in FIG. 23 corresponds essentially to that shown in FIG. 14, and the measurement system shown in FIG. 24 corresponds essentially to the measurement system illustrated in FIG. 15, except that the measurement system is applied according to FIG. 18 and according to the description for FIG. 22. In contrast to FIG. 22, the embodiment shown in FIG. 24 is also suited for measuring pipetted blood to which substances have been added, for example, or which has been otherwise manipulated, or for measuring when only a small quantity of blood (less than 500 μL, for example) is available for a control measurement.

Using the exemplary embodiments explained in FIGS. 3 through 24, the detection of the platelet function of the primary hemostasis may also be carried out in such a way that the measured pressure is maintained at a desired value by back-coupling, and the quantity of blood flow through the capillary is determined as a measure of the aggregation or coagulation of the thrombocytes (German Patent Application 35 41 057 A1).

In addition, in the exemplary embodiments shown in FIGS. 3 through 24 it is possible to carry out the detection procedure in such a way that the change in pressure which occurs during the continued addition of the particular flow path into reaction device 39 is measured at specified time intervals, and that the volumetric flow in each case is altered so that it corresponds to a predetermined function.

The pressure may also be held constant during the predetermined time intervals, and later, when the volumetric flow has fallen by a certain amount, the pressure may be readjusted until it corresponds to the predetermined function (German Patent Application 196 17 407 A1)

A novel method according to the invention is preferably used in which, depending on the pressure measured in pressure gauge chamber 3, the volumetric flow of the blood to be examined is adjusted by reaction device 39 in such a way that a predetermined shear rate or shear force characteristic curve is achieved, and the shear rate or the shear force is preferably held constant.

For clinical analysis, the flow volume and/or the volumetric flow present at the time may be used after a predetermined measuring time has elapsed, or, at a predetermined flow volume the elapsed time and/or the volumetric flow present at the time may be used, or, at a predetermined flow volume the elapsed time and/or the flow volume present at the time may be used. Similarly, the pressure rise after a predetermined time, or the elapsed time after specifying a pressure rise for the parameter formation, may be used.

The volumetric flow is adjusted according to the following relationship:

Volume stream $$V' = \frac{2\gamma^4 l^3 \eta^3 \pi}{\Delta p^3}$$

where the terms have the following meanings:
V' is the volumetric flow of the blood to be examined which flows through the reaction device, in particular through the shear opening;
$\Delta p$ is the pressure measured in the pressure gauge chamber;
l is the length of the flow path in the aperture, in particular in the shear opening;
$\eta$ is the viscosity of the blood to be examined;
$\pi$ is 3.14; and
$\gamma$ is the shear rate.

Control of the measurement system, in particular of the piston movement, may be carried out in such a way that the blood flow proceeds along a predetermined characteristic curve for the shear rate or shear force.

In FIG. 26 a nonlinearly rising shear force characteristic curve is illustrated by a dashed/dotted line, and a linearly falling characteristic curve is illustrated by a dashed line. The shape of the particular characteristic curve for the shear rate (1/s) or for the shear force (N/m²) may optionally be selected depending on the diagnosis being made for which the measurement is carried out. It is preferred to select a constant characteristic curve (solid line in FIG. 26) for a specified shear rate or shear force. For rising flow pressure resulting from deposition or aggregation of thrombocytes in the reaction opening, for example, the desired characteristic curve is obtained by controlling the piston movement according to the above-referenced formula.

FIG. 25 shows parameter-forming quantities, where dashed/dotted line 1 represents the time limitation for the volumetric flow, represented by dashed line 3, and for the flow volume, represented by solid line 4, whose values, determined by the time limitation, form measurement parameters. Or, if dashed line 3 representing the volumetric flow approaches zero, the measurement time indicated by line 2 is obtained as the measurement parameter, and as soon as its predetermined value is reached, the value for the flow volume represented by solid line 4, or alternatively, the value of the flow volume represented by solid line 4, forms the time represented by dashed/dotted line 1. These parameters are formed by the coagulation reaction of the global, in particular the primary, hemostasis, which among other reactions arise due to the effect of a shear quantity from a predetermined characteristic curve. The shear quantity follows a predetermined characteristic curve. These described parameters may be formed in the exemplary embodiments shown in FIGS. 2 through 24.

FIG. 27 shows the volumetric flow normalized to 1 at 5 mbar as a function of the pressure difference dp for regulation of the volumetric flow, depending on dp in the reaction opening, while a constant shear rate is specified.

FIGS. 28 and 29 show measurement results, including the pressure curve, during examination of the coagulation function of the global, in particular the primary, hemostasis, when the volumetric flow is regulated depending on the change in pressure in the reaction opening, while a constant shear rate is specified according to FIG. 27. The sealing time and the sealing volume are measurement values for clinical analysis. In FIG. 28, the volumetric flow passes through in 196 seconds, and a flow volume goes from 310.9 µL to zero.

In FIG. 29, there is hardly any deposition of platelets in the reaction opening due to the platelet-inhibiting effect of ASA (acetylsalicylic acid). The measurement limits are not reached because of the pharmacological effect on the platelet function.

LIST OF REFERENCE NUMBERS

1 Piston-cylinder system
2 Storage vessel
3 Pressure gauge chamber
4 Piston
5 Reaction opening
6 Boundary surface (opening)
7 Reaction opening (aperture)
8 Pressure line (hollow needle)
9 Pressure gauge (pressure sensor)
10 Blood collection chamber
11 Central flow opening
12 Working chamber of conveyor device
13 Coupling
14 Insert
15 Storage chamber
16 Tube
17 Electrical drive device (Electric motor)
18 Control unit
19 Lifting magnet
20 Bleeder valve
21 Flow opening
22 Syringe adapter
23 Heating sleeve
24 Locking and spacing bar
25 Cylinder (measuring cylinder)
26 Sealing insert
27 Feed opening
28 Thrombocyte deposition
29 Boundary surface on insert
30 Boundary surface on vessel base
31 Vessel base
32 Surface on insert
33 Working surface
34 Partition 35 Bioactive coating
36 Piston-cylinder system
37 Container wall
38 Common housing
39 Reaction device
40 Cylinder
41 Pressure gauge line
42 Needle end
43 Hollow needle (cannula)
44 Boundary bars
45 Withdrawal syringe
46 Shear opening
47 Free needle end
48 Nonporous coating
49 Porous coating
50 Intermediate base
51 Support surface (vessel base)
52 Impression (in insert)
53 Impression (in vessel base)
54 Support surface (intermediate base)
55 Hollow needle
56 Sealing collar
57 Catheter
58 Level sensor
59 Syringe cylinder
60 Cannula adapter
61 Ventilation/bleeding
62 Air pocket
63 Converter
64 Housing
65 Container
66 Sealing element
67 Blood sensor
68 Stop bar
69 Sealing wall (housing 64)
70 Porous layer

KEY FOR FIGURES

FIG. 25
Volumenfluβ=Volumetric flow
Volume=Volume
Zeit=Time
FIG. 26
Scherrate=Shear rate
Scherkraft=Shear force
Druck=Pressure
FIG. 27
Caption: Regulation of the volumetric flow depending on dp in the reaction opening (sealing zone), at a specified constant shear rate
Volumenfluβ V' normiert=Volumetric flow V' auf 1 bei 5 mbar normalized to 1 at 5 mbar
Druckunterschied=Pressure difference
FIG. 28
[Text is illegible]
FIG. 29

[Text is illegible]

The invention claimed is:

1. A device for examining properties of global, including primary, hemostasis functions in whole blood or platelet-rich plasma, comprising:
    a storage chamber for the blood or plasma to be examined:
    a reaction device having at least one reaction opening via which blood or plasma to be examined is transported;
    a conveyor device for transport of the blood or plasma through the reaction device; and
    a collection chamber for collecting the blood or plasma transported through the reaction device, wherein the at least one reaction opening is formed in a partition made of a nonporous material which is provided with a bioactive coating on at least one of two partition surfaces thereof and/or on the respective boundary surface of the reaction opening.

2. A device according to claim 1, wherein the diameter of the reaction opening is approximately 0.100 to 0.500 mm.

3. A device according to claim 1, wherein a tube or hollow needle in the reaction device which acts as at least one of a feed opening, and a shear opening is provided upstream from the reaction opening.

4. A device according to claim 1, wherein a coating comprising at least one of erythrocytes and leucocytes, including at least one of blood type O and contained von Willebrand factor, is provided in a region of the reaction opening or boundary surface.

5. A method for detecting global hemostasis function, including primary hemostasis, comprising;
    conveying blood to be examined from a storage chamber under predetermined flow conditions through at least one reaction opening of a reaction device, when blood components are deposited on the reaction surfaces under the action of shear forces in the at least one reaction opening;
    measuring a variable pressure;
    wherein, before the variable pressure measurement is begun, blood viscosity is determined;
    adjusting the volumetric flow of the blood conveyed through the reaction device depending on the respective measured pressure such that the shear rate or the shear force which acts in at least one reaction opening follows a predetermined characteristic curve for the shear rate or shear force;
    wherein said characteristic curve is selected depending on the diagnosis to be made.

6. A method according to claim 5, wherein a pressure rise at the end of a predetermined time or a time until a specified pressure is reached is used for clinical evaluation.

7. A method according to claim 5, wherein the volumetric flowrate is also adjusted, depending on said blood viscosity.

8. A method according to claim 7, wherein the viscosity determination is carried out in the reaction device.

* * * * *